United States Patent [19]

Schwarte

[11] 4,352,759

[45] Oct. 5, 1982

[54] RECOVERY OF HIGH PURITY N-ACYL TAURINE IN HIGH YIELD

[76] Inventor: Erwin Schwarte, 200 Glen Rd., Mountainside, N.J. 07092

[21] Appl. No.: 258,840

[22] Filed: Apr. 29, 1981

[51] Int. Cl.³ .......................................... C07C 143/90
[52] U.S. Cl. .................................................. 260/401
[58] Field of Search ........................... 260/513 N, 401

[56] References Cited

U.S. PATENT DOCUMENTS

| | | | |
|---|---|---|---|
| 2,844,610 | 7/1958 | Freudenberg | 260/404 |
| 2,844,611 | 7/1958 | Freudenberg | 260/404 |
| 4,071,543 | 1/1978 | Bohhmke | 260/401 |
| 4,233,229 | 11/1980 | Chakrabarti | 260/513 N |

Primary Examiner—Arthur P. Demers

[57] ABSTRACT

This invention is directed to an improved method of recovering high purity N-acyl taurine in high yield. The recovery process involves solubilizing crude N-acyl taurine reaction product in a predetermined aqueous-alkanol solvent medium at an elevated temperature, then cooling the solution to a lower temperature whereat high purity N-acyl taurine crystallizes in high yield while salt and other impurities remain in solution, and thereafter filtering the crystalline material.

6 Claims, No Drawings

RECOVERY OF HIGH PURITY N-ACYL TAURINE IN HIGH YIELD

BACKGROUND OF THE INVENTION

1. Field of the Invention

This invention relates to an improved method of recovering high purity N-acyl taurines in high yield.

2. Description of the Prior Art

The Schotten-Baumann reaction is a well-known and highly useful means for acylating taurine compounds by reaction therewith of a carboxylic acid chloride in the presence of alkali. This reaction may be illustrated by the following equation:

$$RCOCl + HNR^1-CHR^2-CHR^2-SO_3M + MOH \rightarrow RCONR^1-CHR^2-CH-R^2-SO_3M + MCl + H_2O$$

wherein:

R is a $C_{5-19}$ hydrocarbon radical,
$R^1$ is H or a $C_{1-6}$ hydrocarbon radical,
$R^2$ is independently H, methyl or ethyl, and
M is alkali metal, e.g. Li, K, or preferably Na.

It is apparent that in the above reaction for the production of Igepon T type (GAF Corporation) anionic surfactants, a considerable quantity of salt is produced as a by-product. The presence of common salt as a contaminant in anionic surface active agents of the "Igepon" type has been recognized not only by the patentees of U.S. Pat. No. 1,932,180, particularly Example 37 and the description thereafter, but also by the teachings of German Pat. No. 664,309, in which an attempt was made to prepare an anionic surface active agent substantially free from salt by reacting the fatty acid amide with a chloroethane sulfonic acid salt in an inert medium capable of dissolving the desired "Igepon", filtering the "Igepon" free from salt and recovering the substantially salt-free "Igepon" by evaporation of the filtrate. Inasmuch as contamination by inorganic salts in commercial "Igepons" is of ever increasing importance due to their corrosive effect in the packaging of heavy duty liquid detergents, adverse hygroscopic and/or taste effect in synthetic soap bars, toothpastes and mold lubricants, and undesirability in certain emulsion polymerization reactions, renewed activity and efforts have been made to devise processes which would yield substantially salt-free products.

A number of patents describe processes for preparation and recovery of such salt-free N-acyl taurines, including U.S. Pat. Nos. 2,987,526; 2,844,610; 2,844,611; and 4,233,229. All of these techniques, however, suffer from the disadvantage that they do not enable the recovery of a high purity product in high yield.

Accordingly, it is the object of this invention to provide an improved method of recovering N-acyl taurines in high yield, relatively and/or substantially free of salt.

SUMMARY OF THE INVENTION

In the present invention, a novel and useful crystallization recovery process for N-acyl taurine of high purity and in high yield from its crude reaction mixture is provided. The process comprises adding an alkanol to a slurry of the aqueous reaction mixture to form an aqueous-alkanol solvent medium having about 50-70% by weight alkanol, 20-35% water and 10-15% solids, heating to a temperature sufficient to solubilize the N-acyl taurine, cooling the solution low enough to crystallize high purity N-acyl taurine in high yield while keeping impurities in solution, and filtering to obtain the product.

This process provides the product in a purity of about 85-95%, which upgrades a 75% purity in the crude mixture, and in a yield of about 90-99%. Subsequent recrystallization, if desired, from alkanol, will further increase the purity somewhat.

DETAILED DESCRIPTION OF THE INVENTION

Any $C_{6-22}$ carboxylic acid chloride (RCOCl) may be employed in the process of this invention. Thus, the acid chloride may be derived from a saturated or unsaturated aliphatic, alicyclic or aliphatic aromatic acid. Acids of this type include caproic acid, isocaproic acid, enanthic acid, δ-methylhexylic acid, caprylic acid, ε-methylheptylic acid, dipropylacetic acid, pelargonic acid, δ-methyloctylic acid, capric acid, η-methylnonylic acid, isoamylisopropylacetic acid, undecylic acid, β-methyldecylic acid, di-tert.-butylmethylacetic acid, lauric acid, diisoamylacetic acid, tridecylic acid, myristic acid, pentadecylic acid, palmitic acid, di-n-heptylacetic acid, margaric acid, stearic acid, di-n-octylacetic acid, nondecylic acid, arachidic acid, behenic acid, γ-hexenoic acid, β-hexenoic acid, pyroterebic acid (4-methyl-β-pentenoic acid), α-ethylcrotonic acid, teracrylic acid, d-citronellic acid, θ-undecylenic acid, oleic acid, elaidic acid, erucic acid, brassidic acid, sorbic acid, stearolic acid, linolic acid, behenolic acid, ricinoleic acid and the like.

In addition to these acids, acids obtained from tall oil, hydrogenated tall oil, hydrogenated tallow, naphthenic, abietic and the like may be employed in the form of their acid chlorides. Alkyl benzoic acids, such as dodecyl benzoic acid, nonyl benzoic acid, alkyl naphthoic acids such as nonyl naphthoic acids and the like may be used in the form of their acid chlorides. Acid mixtures from various natural plant and animal oils, such as olive, tallow, castor, peanut, coconut, soybean, cottonseed, linseed, palm, corn, and the like may also be employed in the form of their acid chlorides.

Coco fatty acid chlorides are preferred, the coconut fatty acids being well known to comprise a mixture in which the $C_{12}$ acids are in highest proportion, lower proportions of $C_{14}$ acids, and decreasing proportions of acids of lower and higher carbon content, mostly saturated.

In the taurine salt reactant, $R^1$ may be H, cyclohexyl, normal or isomeric hexyl, amyl, butyl or propyl, ethyl, or preferably methyl. Examples of suitable taurines include:

| | |
|---|---|
| Taurine | N—butyl taurine |
| Ditaurine | N—isobutyl taurine |
| N—methyl taurine | N—tert.-butyl taurine |
| N—methyl ditaurine | N—amyl taurine |
| N—ethyl taurine | N—isoamyl taurine |
| N—propyl taurine | N—isopropyl taurine |

The salts of the foregoing taurines or 2-aminoalkanesulfonic acids are readily prepared by neutralization thereof with an equivalent amount of potassium or preferably sodium hydroxide or carbonate. Such salts may be reacted in substantially 100% form or in the form of an aqueous slurry or paste. For example, the taurine salt, such as the N-methyl taurine sodium salt, is commercially produced as an approximately 65% aqueous paste which is difficult and/or expensive to dehydrate and is hence preferably employed in the form of the paste, i.e. in the form of an approximately 60–70% aqueous solution (i.e. paste).

Similarly, the alkali metal hydroxide reactant MOH may be employed in 100% powder, flake or other dry form, or in the form of an aqueous solution. A fairly concentrated aqueous solution, e.g. of about 40–60%, preferably about 50%, concentration is often preferred to expedite admixture and solubilization in the reaction medium.

A slight excess, e.g. up to about 5% molar excess, of the acid chloride, or more preferably the taurine salt reactant may be employed to assure a more complete reaction. Any elevated temperature may be employed in carrying out the reaction, as for example from about 30° C. up to reflux, although temperatures of about 30° C. to about 45° C., preferably about 35° C. to about 40° C., are more desirable to avoid undue discoloration of the product and the like. The pH of the reaction medium should be maintained over about 9, preferably up to about 10.5.

The order of addition of the reactants to the reactor is not critical, but in general it is preferred to first dissolve the taurine salt reactant in water and caustic medium and then gradually add the acid chloride reactant while agitating and maintaining the pH and temperature of the reaction medium as described above. The alkali metal hydroxide may be all dissolved in the initial solution of the taurine salt in water medium, or only a portion thereof so dissolved with the remainder added to the reaction medium along with the acid chloride reactant, or more preferably all added gradually along with the acid chloride reactant.

After all the reactants and alkali metal hydroxide have been added to the reaction medium, it is stirred at the indicated reaction temperatures for an additional period, e.g. up to about 1 or 2 hours, to assure completion of the reaction, indicated for example by cessation of change in pH.

After completion of the reaction, an aqueous slurry of the crude acyl taurine is obtained which usually comprises about 32% by weight solids, of which ¾ is acyl taurine and ¼ are impurities, principally salt. The crude taurine at this point has a purity of about 75%, which is upgraded in the crystallization process of the invention.

Accordingly, to the crude aqueous slurry of N-acyl taurine and salt is added a $C_1$–$C_4$ alkanol which provides an aqueous-alkanol medium having a defined relative percentage, by weight, of alkanol and water. Thereby, the N-acyl taurine product can be crystallized from the aqueous-alkanol medium while the salts and other impurities, such as fatty acids, remain in solution. Suitably, alkanol is added to the crude, aqueous reaction product mixture to provide an aqueous-alkanol medium comprising about 50 to 70% by weight alkanol and about 20 to 35% water. The remaining constituent of the mixture is solids, constituting about 10 to 15% of the mixture, that is, N-acyl taurine and salts, in the aforementioned proportions. In the preferred embodiment of the invention, a medium of about 63.8% methanol, 24.6% water and 11.6% solids is used.

The crude aqueous-alkanol product mixture then is heated to reflux (70°–75° C.) and held for 2 hours to solubilize all the solids. Then the mixture is cooled to 0°–5° C. and held for another 2 hours, whereupon high purity, N-acyl taurine crystallizes out of solution in high yield. The salt and other impurities remain in solution. The product is filtered and washed several times with methanol. The filtrate containing the impurities is discarded.

The high purity product thus-obtained by the recovery process of the invention may be further purified, if desired, by conventional recrystallization from alkanol. In recrystallization, unlike the crystallization step, any remaining salt impurities will appear as solids even in hot alkanol while the product is present in solution. Hot filtration removes these solid impurities, upon cooling the filtrate to 0°–5° C., N-acyl taurine crystallizes out.

The $C_{1-4}$ alkanol employed in the instant process may be normal or isomeric butanol or propanol, ethanol, or preferably methanol, or any mixture thereof.

The following example is only illustrative of a preferred embodiment of this invention and is not to be regarded as limitative. All amounts and proportions referred to herein and in the appended claims are by weight unless otherwise indicated.

EXAMPLE 1

A. Preparation of Crude N-Acyl Taurine

Charge
  2,655 lbs. (100%) methyl taurine
  12,645 lbs. water
    Stir ½ hr.
Add 4000 lbs. 25% sodium hydroxide
    Stir 1 hr.
Add at 50°–55° C. while stirring 5000 lbs. coco fatty acid chloride
    Stir 1 hr. at 50°–55° C.
    Heat to 80° C.
Discharge 28,000 lbs. crude product, as aqueous slurry ("A")

B. Recovery of Purified N-Acyl Taurine

Add
  3,000 lbs. Methanol
  1,700 lbs. "A"
    Heat to reflux (70°–75° C.) and hold 2 hrs.
    Cool to 0°–5° C. and hold 2 hrs.
    Filter cold
    Wash 2X with 200 lbs. Methanol at 0°–5° C.
    Press cake dry
    408 lbs. product (95% purity) ("B")

C. Recrystallization of Purified N-Acyl Taurine

Add 3,000 lbs. of Methanol to "B"
    Heat to reflux (70°–75° C.) and hold for ½ hr.
    Filter hot
    Cool mother liquor to 0°–5° C., and hold 2 hrs.
    Filter cold and wash 2X with 200 lbs. Methanol at 0°–5° C.
    Dry press case
    388 lbs. product (98% purity)

While there are above disclosed but a limited number of embodiments of the process of the invention it is possible to provide still other embodiments without departing from the inventive concept herein disclosed, and it is therefore desired that only such limitations be imposed upon the appended claims as are stated therein or required by the prior art.

What is claimed is:

1. A process for recovering an N-acyl taurine in high yield and substantially free of alkali metal chloride salt from a crude product mixture thereof resulting from reacting, in an aqueous medium at temperatures ranging from about 30° C. up to reflux, 1 mole of a $C_6$–$C_{22}$ carboxylic acid chloride with 1 mole of a taurine salt of the formula $$HNR^1\text{—}CHR^2\text{—}CHR^2\text{—}SO_3M$$

wherein
- $R^1$ is H or a $C_{1-6}$ hydrocarbon radical,
- $R^2$ is independently H, methyl or ethyl, and
- M is alkali metal, in the presence of about 1 mole of alkali metal hydroxide, which comprises the steps of:
adding a $C_{1-4}$ alkanol to the reacted mixture to form an aqueous-alkanol mixture comprising from about 50 to 70% by weight alkanol, about 20 to 35% water and about 10 to 15% solids, heating to a temperature sufficient to solubilize the N-acyl taurine and salts, then cooling the solution low enough to crystallize a high purity N-acyl taurine product in high yield while keeping said salt and other impurities in solution, and filtering the crystalline material to recover the thus-purified product.

2. The method of claim 1 including the additional step of recrystallizing the purified product from substantially pure alkanol.

3. The method of claim 1 wherein said alkanol is methanol.

4. The method of claim 1 wherein said crude reaction product mixture comprises about 32% by weight solids, of which about ¾ is N-acyl taurine and ¼ is salts and other impurities, and about 68% water.

5. The method according to claim 1 wherein said N-acyl taurine is recovered in a yield of 90–99%, and a purity of about 85–95%.

6. The method of claim 1 wherein said aqueous-alkanol medium comprises about 24.6% water, 63.8% methanol and 11.6% solids.

* * * * *